US006379708B1

(12) United States Patent
Howell et al.

(10) Patent No.: US 6,379,708 B1
(45) Date of Patent: Apr. 30, 2002

(54) METHOD FOR ENHANCING IMMUNE RESPONSES IN MAMMALS

(75) Inventors: Mark Douglas Howell; Cheryl Lynn Selinsky; Leland Charles Leber, all of Ft. Collins, CO (US)

(73) Assignees: Cytologic, LLC; Colorado State University Research Foundation, both of Fort Collins, CO (US)

( * ) Notice: Subject to any disclaimer, the term of this patent is extended or adjusted under 35 U.S.C. 154(b) by 0 days.

(21) Appl. No.: 09/444,144

(22) Filed: Nov. 20, 1999

(51) Int. Cl.[7] .............................................. A61K 35/14
(52) U.S. Cl. ................ 424/529; 530/388.25; 530/388.1
(58) Field of Search .......................... 424/529; 530/412, 530/413, 388.1, 388.25, 389.1, 389.7, 391.3, 300; 436/535, 538, 541; 435/2

(56) References Cited

U.S. PATENT DOCUMENTS

| 4,708,713 A | | 11/1987 | Lentz |
| 6,017,527 A | * | 1/2000 | Maraskovsky et al. |
| 6,231,536 B1 | | 5/2001 | Lentz |

FOREIGN PATENT DOCUMENTS

| EP | 0 184 040 B1 | | 11/1986 |
| JP | 02045064 | * | 2/1990 |
| WO | WO 91/0996 | * | 7/1991 |
| WO | WO 96/16666 | * | 6/1996 |

OTHER PUBLICATIONS

Rudikoff et al., Proc. Natl. Acad. Sci. USA 79:1979–1983, 1982.*

Amit et al., Science 233:747–753, 1986.*

Panka et al., Proc. Natl. Acad. Sci. USA 85:3080–3084, 1988.*

Aderka, D., et al., "Increased serum levels of soluble receptors for tumor necrosis factor in cancer patients", *Cancer Research*, vol. 51, pp. 5602–5607 (1991).

Elsasser–Beile, U., et al., "Increased plasma concentrations for type I and II tumor necrosis factor receptors and IL–2 receptors in cancer patients", *Tumor Biology*, vol. 15, pp. 17–24 (1994).

Digel, W., et al., "High levels of circulating soluble receptors for tumor necrosis factor in hairy cell leukemia and type B chronic lymphocytic leukemia", *Journal of Clinical Investigation*, vol. 89, pp. 1690–1693 (1992).

Lentz, M. R., "Continuous whole blood ultrapheresis procedure in patients with metastatic cancer", *Journal of Biological Response Modifiers*, vol. 8, pp. 511–527 (1989).

Lentz, M. R., "The role of therapeutic apheresis in the treatment of cancer: a review", *Therapeutic Apheresis*, vol. 3, pp. 40–49 (1999).

Lentz, R., et al., "Low molecular weight protein apheresis and regression of breast cancer", *Japanese Journal of Apheresis*, vol. 15, pp. 107–114 (1997).

Kessler, S. B., "Adsorptive plasma treatment: optimization of extracorporeal devices and systems", *Blood Purification*, vol. 11, pp. 150–157 (1993).

Selinsky, C. L., et al., "Multifaceted inhibition of anti–tumor immune mechanisms by soluble tumour necrosis factor receptor type I", *Immunology*, vol. 94, pp. 88–93 (1998).

Selinsky, C. L. and Howell, M. D., "Soluble tumor necrosis factor receptor type I enhances tumor development and persistence in vivo", *Cellular Immunology*, in press (2000).

* cited by examiner

Primary Examiner—Sheela Huff
Assistant Examiner—Larry R. Helms
(74) Attorney, Agent, or Firm—Sheridan Ross P.C.

(57) ABSTRACT

The present invention provides a method for enhancing an immune response in a mammal to facilitate the elimination of a chronic pathology. The method involves the removal of immune system inhibitors from the circulation of the mammal, thus, enabling a more vigorous immune response to the pathogenic agent. The removal of immune system inhibitors is accomplished by contacting biological fluids of a mammal with one or more binding partner(s) capable of binding to and, thus, depleting the targeted immune system inhibitor(s) from the biological fluids. Particularly useful in the invention is an absorbent matrix composed of an inert, biocompatible substrate joined covalently to a binding partner, such as an antibody, capable of specifically binding to the targeted immune system inhibitor.

44 Claims, 3 Drawing Sheets

METHOD FOR ENHANCING IMMUNE RESPONSES IN MAMMALS

This invention relates generally to the field of immunotherapy and, more specifically, to methods for enhancing host immune responses.

BACKGROUND OF THE INVENTION

The immune system of mammals has evolved to protect the host against the growth and proliferation of potentially deleterious agents. These agents include infectious microorganisms such as bacteria, viruses, fungi, and parasites which exist in the environment and which, upon introduction to the body of the host, can induce varied pathological conditions. Other pathological conditions may derive from agents not acquired from the environment, but rather which arise spontaneously within the body of the host. The best examples are the numerous malignancies known to occur in mammals. Ideally, the presence of these deleterious agents in a host triggers the mobilization of the immune system to effect the destruction of the agent and, thus, restore the sanctity of the host environment.

The destruction of pathogenic agents by the immune system involves a variety of effector mechanisms which can be grouped generally into two categories: innate and specific immunity. The first line of defense is mediated by the mechanisms of innate immunity. Innate immunity does not discriminate among the myriad agents that might gain entry into the host's body. Rather, it responds in a generalized manner that employs the inflammatory response, phagocytes, and plasma-borne components such as complement and interferons. In contrast, specific immunity does discriminate among pathogenic agents. Specific immunity is mediated by B and T lymphocytes and it serves, in large part, to amplify and focus the effector mechanisms of innate immunity.

The elaboration of an effective immune response requires contributions from both innate and specific immune mechanisms. The function of each of these arms of the immune system individually, as well as their interaction with each other, is carefully coordinated, both in a temporal/spatial manner and in terms of the particular cell types that participate. This coordination results from the actions of a number of soluble immunostimulatory mediators or "immune system stimulators" (Reviewed in, Trinchieri, et al., *J. Cell. Biochem.* 53:301–308 (1993)). Certain of these immune system stimulators initiate and perpetuate the inflammatory response and the attendant systemic sequelae. Examples of these include, but are not limited to, the proinflammatory mediators tumor necrosis factors $\alpha$ and $\beta$, interleukin-1, interleukin-6, interleukin-8, interferon-$\gamma$, and the chemokines RANTES, macrophage inflammatory proteins 1-$\alpha$ and 1-$\beta$, and macrophage chemotactic and activating factor. Other immune system stimulators facilitate interactions between B and T lymphocytes of specific immunity. Examples of these include, but are not limited to, interleukin-2, interleukin-4, interleukin-5, interleukin-6, and interferon-$\gamma$. Still other immune system stimulators mediate bidirectional communication between specific immunity and innate immunity. Examples of these include, but are not limited to, interferon-$\gamma$, interleukin-1, tumor necrosis factors $\alpha$ and $\beta$, and interleukin-12. All of these immune system stimulators exert their effects by binding to specific receptors on the surface of host cells, resulting in the delivery of intracellular signals that alter the function of the target cell. Cooperatively, these mediators stimulate the activation and proliferation of immune cells, recruit them to particular anatomical sites, and permit their collaboration in the elimination of the offending agent. The immune response induced in any individual is determined by the particular complement of immune system stimulators produced, and by the relative abundance of each.

In contrast to the immune system stimulators described above, the immune system has evolved other soluble mediators that serve to inhibit immune responses (Reviewed in, Arend, W. P., *Adv. Int. Med.* 40:365–394 (1995)). These "immune system inhibitors" provide the immune system with the ability to dampen responses in order to prevent the establishment of a chronic inflammatory state with the potential to damage the host's tissues. Regulation of host immune function by immune system inhibitors is accomplished through a variety of mechanisms as described below.

First, certain immune system inhibitors bind directly to immune system stimulators and, thus, prevent them from binding to plasma membrane receptors on host cells. Examples of these types of immune system inhibitors include, but are not limited to, the soluble receptors for tumor necrosis factors $\alpha$ and $\beta$, interferon-$\gamma$, interleukin-1, interleukin-2, interleukin-4, interleukin-6, and interleukin-7.

Second, certain immune system inhibitors antagonize the binding of immune system stimulators to their receptors. By way of example, interleukin-1 receptor antagonist is known to bind to the interleukin-1 membrane receptor. It does not deliver activation signals to the target cell but, by virtue of occupying the interleukin-1 membrane receptor, blocks the effects of interleukin-1.

Third, particular immune system inhibitors exert their effects by binding to receptors on host cells and signalling a decrease in their production of immune system stimulators. Examples include, but are not limited to, interferon-$\beta$, which decreases the production of two key proinflammatory mediators, tumor necrosis factor-$\alpha$ and interleukin-1 (Coclet-Ninin et al., *Eur. Cytokine Network* 8:345–349 (1997)), and interleukin-10, which suppresses the development of cell-mediated immune responses by inhibiting the production of the immune system stimulator, interleukin-12 (D'Andrea, et al., *J. Exp. Med.* 178:1041–1048 (1993)). In addition to decreasing the production of immune system stimulators, certain immune system inhibitors also enhance the production of other immune system inhibitors. By way of example, interferon-$\alpha_{2b}$ inhibits interleukin-1 and tumor necrosis factor-$\alpha$ production and increases the production of the corresponding immune system inhibitors, interleukin-1 receptor antagonist and soluble receptors for tumor necrosis factors $\alpha$ and $\beta$ (Dinarello, C. A., *Sem. in Oncol.* 24(3 Suppl. 9):81–93 (1997)).

Fourth, certain immune system inhibitors act directly on immune cells, inhibiting their proliferation and function, thereby, decreasing the vigor of the immune response. By way of example, transforming growth factor-$\beta$ inhibits a variety of immune cells, and significantly limits inflammation and cell-mediated immune responses (Reviewed in, Letterio and Roberts, *Ann. Rev. Immunol.* 16:137–161 (1998)). Collectively, these various immunosuppressive mechanisms are intended to regulate the immune response, both quantitatively and qualitatively, to minimize the potential for collateral damage to the host's own tissues.

In addition to the inhibitors produced by the host's immune system for self-regulation, other immune system inhibitors are produced by infectious microorganisms. For example, many viruses produce molecules which are viral homologues of host immune system inhibitors (Reviewed in, Spriggs, M. K., *Ann. Rev. Immunol.* 14:101–130 (1996)). These include homologues of host complement inhibitors, interleukin-10, and soluble receptors for interleukin-1, tumor necrosis factors α and β, and interferons α, β and γ. Similarly, helminthic parasites produce homologues of host immune system inhibitors (Reviewed in, Riffkin, et al., *Immunol. Cell Biol.* 74:564–574 (1996)), and several bacterial genera are known to produce immunosuppressive products (Reviewed in, Reimann, et al., *Scand. J. Immunol.* 31:543–546 (1990)). All of these immune system inhibitors serve to suppress the immune response during the initial stages of infection, to provide advantage to the microbe, and to enhance the virulence and chronicity of the infection.

A role for host-derived immune system inhibitors in chronic disease also has been established. In the majority of cases, this reflects a polarized T cell response during the initial infection, wherein the production of immunosuppressive mediators (i.e., interleukin-4, interleukin-10, and/or transforming growth factor-β dominates over the production of immunostimulatory mediators (i.e., interleukin-2, interferon-γ, and/or tumor necrosis factor-β) (Reviewed in, Lucey, et al., *Clin. Micro. Rev.* 9:532–562 (1996)). Overproduction of immunosuppressive mediators of this type has been shown to produce chronic, non-healing pathologies in a number of medically important diseases. These include, but are not limited to, diseases resulting from infection with: 1) the parasites, *Plasmodium falciparum* (Sarthou, et al. *Infect. Immun.* 65:3271–3276 (1997)), Trypanosoma cruzi (Reviewed in, Laucella, et al. *Revista Argentina de Microbiologia* 28:99–109 (1996)), Leishmania major (Reviewed in, Etges and Muller, *J. Mol. Med.* 76:372–390 (1998)), and certain helminths (Riffkin, et al., supra); 2) the intracellular bacteria, *Mycobacterium tuberculosis* (Baliko, et al., FEMS *Immunol. Med. Micro.* 22:199–204 (1998)), *Mycobacterium avium* (Bermudez and Champsi, *Infect. Immun.* 61:3093–3097 (1993)), *Mycobacterium leprae* (Sieling, et al. *J. Immunol.* 150:5501–5510 (1993)), *Mycobacterium bovis* (Kaufmann, et al., *Ciba Fdn. Symp.* 195:123–132 (1995)), *Brucella abortus* (Fernandes and Baldwin, *Infect. Immun.* 63:1130–1133 (1995)), and *Listeria monocytogenes* (Blauer, et al., *J. Interferon Cytokine Res.* 15:105–114 (1995)); and, 3) the intracellular fungus, *Candida albicans* (Reviewed in, Romani, et al., *Immunol. Res.* 14:148–162 (1995)). The inability to spontaneously resolve infection is influenced by other host-derived immune system inhibitors as well. By way of example, interleukin-1 receptor antagonist and the soluble receptors for tumor necrosis factors α and β are produced in response to interleukin-1 and tumor necrosis factor α and/or β production driven by the presence of numerous infectious agents. Examples include, but are not limited to, infections by *Plasmodium falciparum* (Jakobsen, et al. *Infect. Immun.* 66:1654–1659 (1998), Sarthou, et al., supra), *Mycobacterium tuberculosis* (Balcewicz-Sablinska, et al., *J. Immunol.* 161:2636–2641 (1998)), and *Mycobacterium avium* (Eriks and Emerson, *Infect. Immun.* 65:2100–2106 (1997)). In cases where the production of any of the aforementioned immune system inhibitors, either individually or in combination, dampens or otherwise alters immune responsiveness before the elimination of the pathogenic agent, a chronic infection may result.

In addition this role in infectious disease, host-derived immune system inhibitors contribute also to chronic malignant disease. Compelling evidence is provided by studies of soluble tumor necrosis factor receptor type I (sTNFRI) in cancer patients. Nanomolar concentrations of sTNFRI are synthesized by a variety of activated immune cells in cancer patients and, in many cases, by the tumors themselves (Aderka et al., *Cancer Res.* 51: 5602–5607 (1991); Adolf and Apfler, *J. Immunol. Meth.* 143: 127–36 (1991)). In addition, circulating sTNFRI levels often are elevated significantly in cancer patients (Aderka, et al., supra; Kalmanti, et al., *Int. J. Hematol.* 57: 147–152 (1993); Elsasser-Beile, et al., *Tumor Biol.* 15: 17–24 (1994); Gadducci, et al., *Anticancer Res.* 16: 3125–3128 (1996); Digel, et al., *J. Clin. Invest.* 89: 1690–1693 (1992)), decline during remission and increase during advanced stages of tumor development (Aderka, et al., supra; Kalmanti, et al., supra; Elsasser-Beile, et al., supra; Gadducci, et al., supra) and, when present at high levels, correlate with poorer treatment outcomes (Aderka, et al., supra). These observations suggest that sTNFRI aids tumor survival by inhibiting anti-tumor immune mechanisms which employ tumor necrosis factors α and/or β (TNF), and they argue favorably for the clinical manipulation of sTNFRI levels as a therapeutic strategy for cancer.

Direct evidence that the removal of immune system inhibitors provides clinical benefit derives from the evaluation of Ultrapheresis, a promising experimental cancer therapy (Lentz, M. R., *J. Biol. Response Modif.* 8: 511–27 (1989); Lentz, M. R., *Ther. Apheresis* 3: 40–49 (1999); Lentz, M. R., *Jpn. J. Apheresis* 16: 107–14 (1997)). Ultrapheresis involves extracorporeal fractionation of plasma components by ultrafiltration. Ultrapheresis selectively removes plasma components within a defined molecular size range, and it has been shown to provide significant clinical advantage to patients presenting with a variety of tumor types. Ultrapheresis induces pronounced inflammation at tumor sites, often in less than one hour post-initiation. This rapidity suggests a role for preformed chemical and/or cellular mediators in the elaboration of this inflammatory response, and it reflects the removal of naturally occurring plasma inhibitors of that response. Indeed, immune system inhibitors of TNF α and β, interleukin-1, and interleukin-6 are removed by Ultrapheresis (Lentz, M. R., *Ther. Apheresis* 3: 40–49 (1999)). Notably, the removal of sTNFRI has been correlated with the observed clinical responses (Lentz, M. R., *Ther. Apheresis* 3: 40–49 (1999); Lentz, M. R., *Jpn. J. Apheresis* 16: 107–14 (1997)).

Ultrapheresis is in direct contrast to more traditional approaches which have endeavored to boost immunity through the addition of immune system stimulators. Preeminent among these has been the infusion of supraphysiological levels of TNF (Sidhu and Bollon, *Pharmacol, Ther.* 57: 79–128 (1993)), and of interleukin-2 (Maas, et al., *Cancer Immunol. Immunother.* 36: 141–148 (1993)), which indirectly stimulates the production of TNF. These therapies have enjoyed limited success (Sidhu and Bollon, supra; Maas, et al., supra) due to the fact: 1) that at the levels employed they proved extremely toxic; and, 2) that each increases the plasma levels of the immune system inhibitor, sTNFRI (Lantz, et al., Cytokine 2: 402–406 (1990); Miles, et al., *Brit. J. Cancer* 66: 1195–1199 (1992)). Together, these observations support the utility of Ultrapheresis as a biotherapeutic approach to cancer—one which involves the removal of immune system inhibitors, rather than the addition of immune system stimulators.

Although Ultrapheresis provides advantages over traditional therapeutic approaches, there are certain drawbacks that limit its clinical usefulness. Not only are immune system inhibitors removed by Ultrapheresis, but other plasma components, including beneficial ones, are removed since the discrimination between removed and retained plasma components is based solely on molecular size. An additional drawback to Ultrapheresis is the significant loss of circulatory volume during treatment, which must be offset by the infusion of replacement fluid. The most effective replacement fluid is an ultrafiltrate produced, in an identical manner, from the plasma of non-tumor bearing donors. A typical treatment regimen (15 treatments, each with the removal of approximately 7 liters of ultrafiltrate) requires over 200 liters of donor plasma for the production of replacement fluid. The chronic shortage of donor plasma, combined with the risks of infection by human immunodeficiency virus, hepatitis A, B, and C or other etiologic agents, represents a severe impediment to the widespread implementation of Ultrapheresis.

Because of the beneficial effects associated with the removal of immune system inhibitors, there exists a need for methods which can be used to specifically deplete those inhibitors from circulation. Such methods ideally should be specific and not remove other circulatory components, and they should not result in any significant loss of circulatory volume. The present invention satisfies these needs and provides related advantages as well.

SUMMARY OF THE INVENTION

The present invention provides a method for stimulating immune responses in a mammal through the depletion of immune system inhibitors present in the circulation of said mammal. The depletion of immune system inhibitors can be effected by removing biological fluids from said mammal and contacting these biological fluids with a binding partner capable of selectively binding to the targeted immune system inhibitor.

Binding partners useful in these methods can be antibodies, both polyclonal or monoclonal antibodies, or fragments thereof, having specificity for a targeted immune system inhibitor. Additionally, binding partners to which the immune system inhibitor naturally binds may be used. Synthetic peptides created to attach specifically to targeted immune system inhibitors also are useful as binding partners in the present methods. Moreover, mixtures of binding partners having specificity for multiple immune system inhibitors may be used.

Figure 1:
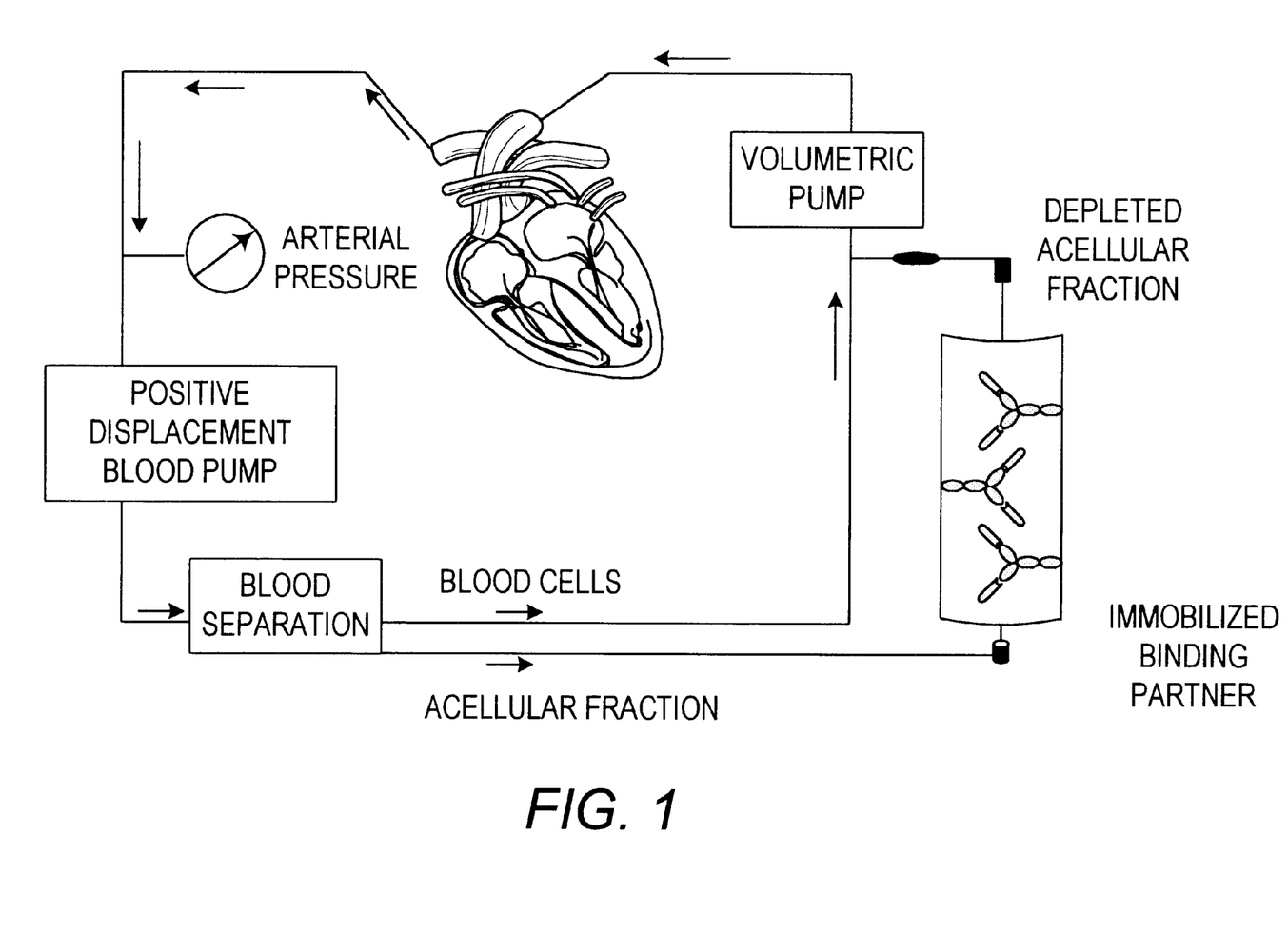
FIG. 1 schematically illustrates the "absorbent matrix" configuration described herein. In this example, blood is removed from the patient and separated into a cellular and an acellular component, or fractions thereof. The acellular component, or fractions thereof, is exposed to the absorbent matrix to effect the binding and, thus, depletion of the targeted immune system inhibitor. The altered acellular component, or fractions thereof, then is returned contemporaneously to the patient.

In a particularly useful embodiment, the binding partner is immobilized previously on a solid support to create an "absorbent matrix" (FIG. 1). The exposure of biological fluids to such an absorbent matrix will permit binding by the immune system inhibitor, thus, effecting a decrease in its abundance in the biological fluids. The treated biological fluid can be returned to the patient. The total volume of biological fluid to be treated and the treatment rate are parameters individualized for each patient, guided by the induction of vigorous immune responses while minimizing toxicity. The solid support (i.e., inert medium) can be composed of any material useful for such purpose, including, for example, hollow fibers, cellulose-based fibers, synthetic fibers, A flat or pleated membranes, silica-based particles, or macroporous beads.

Figure 2:
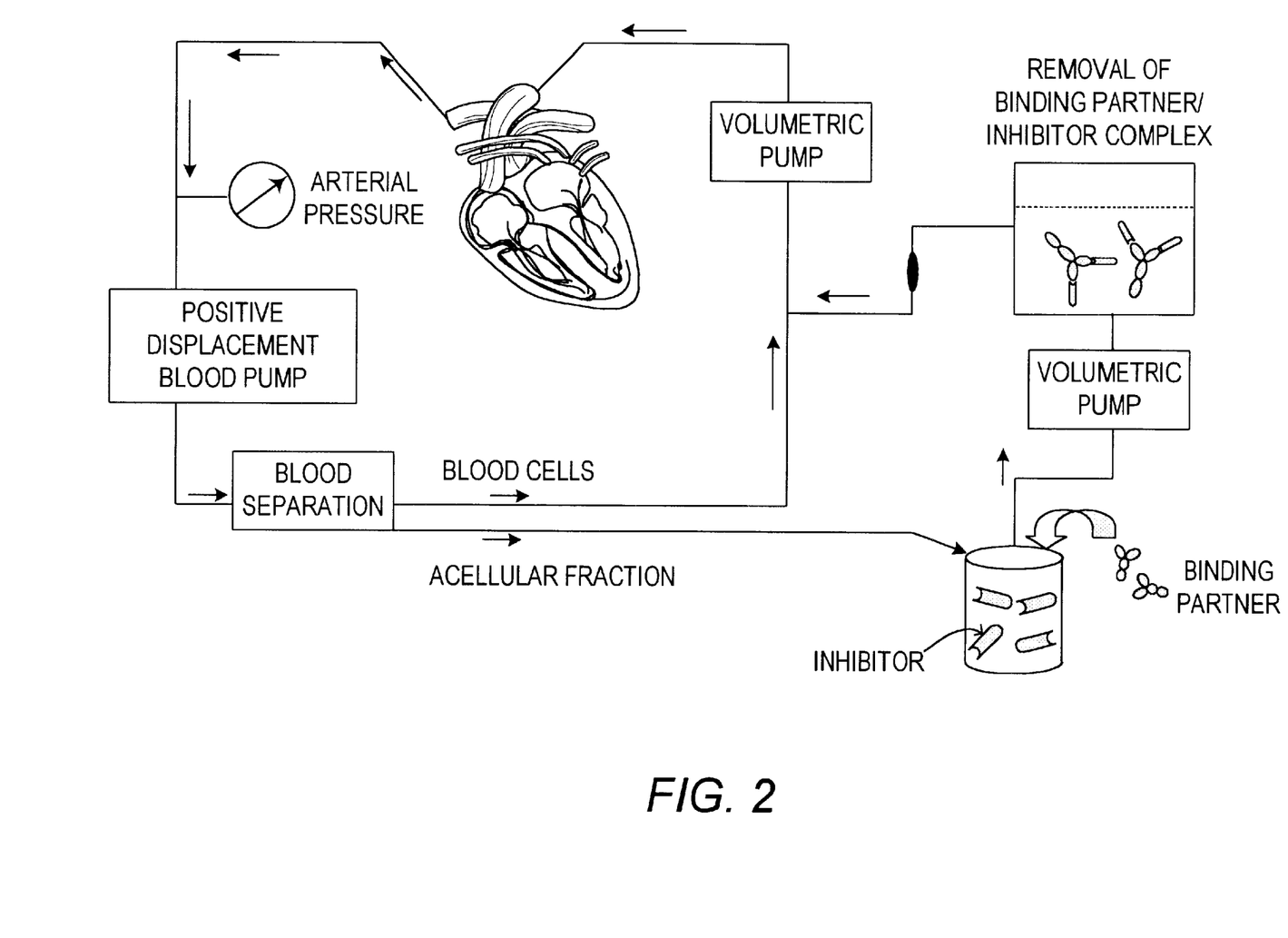
FIG. 2 schematically illustrates the "stirred reactor" configuration described herein. In this example, blood is removed from the patient and separated into a cellular and an acellular component, or fractions thereof. A binding partner is added to the acellular component, or fractions thereof. Subsequently, the binding partner/immune system inhibitor complex is removed by mechanical or by chemical or biological means from the acellular component, or fractions thereof, and the altered biological fluid is returned contemporaneously to the patient.

In another embodiment, the binding partner can be mixed with the biological fluid in a "stirred reactor" (FIG. 2). The binding partner-immune system inhibitor complex then can be removed by mechanical or by chemical or biological means, and the altered biological fluid can be returned to the patient.

The present invention also provides apparatus incorporating either the absorbent matrix or the stirred reactor.

DETAILED DESCRIPTION OF THE INVENTION

The present invention provides novel methods to reduce the levels of immune system inhibitors in the circulation of a host mammal, thereby, potentiating an immune response capable of resolving a pathological condition. By enhancing the magnitude of the host's immune response, the invention avoids the problems associated with the repeated administration of chemotherapeutic agents which often have undesirable side effects (e.g., chemotherapeutic agents used in treating cancer).

The methods of the present invention generally are accomplished by: (a) obtaining a biological fluid from a mammal having a pathological condition; (b) contacting the biological fluid with a binding partner capable of selectively binding to a targeted immune system inhibitor to produce an altered biological fluid having a reduced amount of the targeted immune system inhibitor; and, thereafter (c) administering the altered biological fluid to the mammal.

As used herein, the term "immune system stimulator" refers to soluble mediators that increase the magnitude of an immune response, or which encourage the development of particular immune mechanisms that are more effective in resolving a specific pathological condition.

As used herein, the term "immune system inhibitor" refers to a soluble mediator that decreases the magnitude of an immune response, or which discourages the development of particular immune mechanisms that are more effective in resolving a specific pathological condition, or which encourages the development of particular immune mechanisms that are less effective in resolving a specific pathological condition. Examples of host-derived immune system inhibitors include interleukin-1 receptor antagonist, transforming growth factor-$\beta$, interleukin-4, interleukin-10, or the soluble receptors for interleukin-1, interleukin-2, interleukin-4, interleukin-6, interleukin-7, interferon-$\gamma$ and tumor necrosis factors $\alpha$ and $\beta$. Immune system inhibitors produced by microorganisms are also potential targets including, for example, complement inhibitors, and homologues of interleukin-10, soluble receptors for interleukin-1, interferons $\alpha$, $\beta$, and $\gamma$, and tumor necrosis factors $\alpha$ and $\beta$. As used herein, the term "targeted"immune system inhibitor refers to that inhibitor, or collection of inhibitors, which is to be removed from the biological fluid by the present method.

As used herein, the term "mammal" can be a human or a non-human animal, such as dog, cat, horse, cattle, pig, or sheep for example. The term "patient" is used synonymously with the term "mammal" in describing the invention.

As used herein, the term "pathological condition" refers to any condition where the persistence, within a host, of an agent, immunologically distinct from the host, is a component of or contributes to a disease state. Examples of such pathological conditions include, but are not limited to those resulting from persistent viral, bacterial, parasitic, and fungal infections, and cancer. Among individuals exhibiting such chronic diseases, those in whom the levels of immune system inhibitors are elevated are particularly suitable for the treatment of the invention. Plasma levels of immune system inhibitors can be determined using methods well-known in the art (See, for example, Adolf and Apfler, supra). Those skilled in the art readily can determine pathological conditions that would benefit from the depletion of immune system inhibitors according to the present methods.

As it relates to the present invention, the term "biological fluid" refers to the acellular component of the circulatory system including plasma, serum, lymphatic fluid, or fractions thereof. The biological fluids can be removed from the mammal by any means known to those skilled in the art, including, for example, conventional apheresis methods (See, Apheresis: *Principles and Practice*, McLeod, B. C., Price, T. H., and Drew, M. J., eds., AABB Press, Bethesda, MD (1997)). The amount of biological fluid to be extracted from a mammal at a given time will depend on a number of factors, including the age and weight of the host mammal and the volume required to achieve therapeutic benefit. As an initial guideline, one plasma volume (approximately 5–7 liters in an adult human) can be removed and, thereafter, depleted of the targeted immune system inhibitor according to the present methods.

As used herein, the term "selectively binds" means that a molecule binds to one type of target molecule, but not substantially to other types of molecules. The term "specifically binds" is used interchangeably herein with "selectively binds".

As used herein, the term "binding partner" is intended to include any molecule chosen for its ability to selectively bind to the targeted immune system inhibitor. The binding partner can be one which naturally binds the targeted immune system inhibitor. For example, tumor necrosis factor α or β can be used as a binding partner for sTNFRI. Alternatively, other binding partners, chosen for their ability to selectively bind to the targeted immune system inhibitor, can be used. These include fragments of the natural binding partner, polyclonal or monoclonal antibody preparations or fragments thereof, or synthetic peptides.

The present invention further relates to the use of various mixtures of binding partners. One mixture can be composed of multiple binding partners that selectively bind to different binding sites on a single targeted immune system inhibitor. Another mixture can be composed of multiple binding partners, each of which selectively binds to a single site on different targeted immune system inhibitors. Alternatively, the mixture can be composed of multiple binding partners that selectively bind to different binding sites on different targeted immune system inhibitors. The mixtures referred to above may include mixtures of antibodies or fragments thereof, mixtures of natural binding partners, mixtures of synthetic peptides, or mixtures of any combinations thereof.

For certain embodiments in which it would be desirable to increase the molecular weight of the binding partner/immune system inhibitor complex, the binding partner can be conjugated to a carrier. Examples of such carriers include, but are not limited to, proteins, complex carbohydrates, and synthetic polymers such as polyethylene glycol.

Additionally, binding partners can be constructed as multifunctional antibodies according to methods known in the art. For example, bifunctional antibodies having two functionally active binding sites per molecule or trifunctional antibodies having three functionally active binding sites per molecule can be made by known methods. As used herein, "functionally active binding sites" refer to sites that are capable of binding to one or more targeted immune system inhibitors. By way of illustration, a bifunctional antibody can be produced that has functionally active binding sites, each of which selectively binds to different targeted immune system inhibitors.

Methods for producing the various binding partners useful in the present invention are well known to those skilled in the art. Such methods include, for example, serologic, hybridoma, recombinant DNA, and synthetic techniques, or a combination thereof.

In one embodiment of the present methods, the binding partner is attached to an inert medium to form an absorbent matrix (FIG. 1). As used herein, the term "inert medium" is intended to include solid supports to which the binding partner(s) can be attached. Particularly useful supports are materials that are used for such purposes including, for example, cellulose-based hollow fibers, synthetic hollow fibers, silica-based particles, flat or pleated membranes, and macroporous beads. Such inert media can be obtained commercially or can be readily made by those skilled in the art. The binding partner can be attached to the inert medium by any means known to those skilled in the art including, for example, covalent conjugation. Alternatively, the binding partner may be associated with the inert matrix through high-affinity, non-covalent interaction with an additional molecule which has been covalently attached to the inert medium. For example, a biotinylated binding partner may interact with avidin or streptavidin previously conjugated to the inert medium.

The absorbent matrix thus produced can be contacted with a biological fluid, or a fraction thereof, through the use of an extracorporeal circuit. The development and use of extracorporeal, absorbent matrices has been extensively reviewed. (See, Kessler, L., *Blood Purification* 11:150–157 (1993)).

In another embodiment, herein referred to as the "stirred reactor" (FIG. 2), the biological fluid is exposed to the binding partner in a mixing chamber and, thereafter, the binding partner/immune system inhibitor complex is removed by means known to those skilled in the art, including, for example, by mechanical or by chemical or biological separation methods. For example, a mechanical separation method can be used in cases where the binding partner, and therefore the binding partner/immune system inhibitor complex, represent the largest components of the treated biological fluid. In these cases, filtration can be used to retain the binding partner and immune system inhibitors associated therewith, while allowing all other components of the biological fluid to permeate through the filter and, thus, to be returned to the patient. In an example of a chemical or biological separation method, the binding partner and immune system inhibitors associated therewith, can be removed from the treated biological fluid through exposure to an absorbent matrix capable of specifically attaching to the binding partner. For example, a matrix constructed with antibodies reactive with mouse immunoglobulins (e.g., goat anti-mouse IgG) would serve this purpose in cases where the binding partner were a mouse monoclonal IgG. Similarly, were biotin conjugated to the binding partner prior to its addition to the biological fluid, a matrix constructed with avidin or streptavidin could be used to deplete the binding partner and immune system inhibitors associated therewith from the treated fluid.

In the final step of the present methods, the treated or altered biological fluid, having a reduced amount of targeted immune system inhibitor, is returned to the patient receiving treatment along with untreated fractions of the biological fluid, if any such fractions were produced during the treatment. The altered biological fluid can be administered to the mammal by any means known to those skilled in the art, including, for example, by infusion directly into the circulatory system. The altered biological fluid can be administered immediately after contact with the binding partner in a contemporaneous, extracorporeal circuit. In this circuit, the biological fluid is (a) collected, (b) separated into cellular and acellular components, if desired, (c) exposed to the binding partner, and if needed, separated from the binding partner bound to the targeted immune system inhibitor, (d) combined with the cellular component, if needed, and (e) readministered to the patient as altered biological fluid. Alternatively, the administration of the altered biological fluid can be delayed under appropriate storage conditions readily determined by those skilled in the art.

It may be desirable to repeat the entire process. Those skilled in the art can readily determine the benefits of repeated treatment by monitoring the clinical status of the patient, and correlating that status with the concentration(s) of the targeted immune system inhibitor(s) in circulation prior to, during, and after treatment.

The present invention further provides novel apparatus for reducing the amount of a targeted immune system inhibitor in a biological fluid. These apparatus are composed of: (a) a means for separating the biological fluid into a cellular component and an acellular component or fraction thereof; (b) an absorbent matrix or a stirred reactor as described above to produce an altered acellular component or fraction thereof; and (c) a means for combining the cellular fraction with the altered acellular component or fraction thereof. These apparatus are particularly useful for whole blood as the biological fluid in which the cellular component is separated either from whole plasma or a fraction thereof.

The means for initially fractionating the biological fluid into the cellular component and the acellular component, or a fraction thereof, and for recombining the cellular component with the acellular component, or fraction thereof, after treatment are known to those skilled in the art. (See, Apheresis: *Principles and Practice*, supra.)

In one specific embodiment, the immune system inhibitor to be targeted is sTNFRI (Seckinger, et al., *J. Biol. Chem.* 264: 11966–73 (1989); Gatanaga, et al., *Proc. Natl. Acad. Sci.* 87: 8781–84 (1990)), a naturally occurring inhibitor of the pluripotent immune system stimulator, TNF. sTNFRI is produced by proteolytic cleavage which liberates the extracellular domain of the membrane tumor necrosis factor receptor type I from its transmembrane and intracellular domains (Schall, et al., *Cell* 61: 361–70 (1990); Himmler, et al., *DNA and Cell Biol.* 9: 705–715 (1990)). sTNFRI retains the ability to bind to TNF with high affinity and, thus, to inhibit the binding of TNF to the membrane receptor on cell surfaces.

The levels of sTNFRI in biological fluids are increased in a variety of conditions which are characterized by an antecedent increase in TNF. These include bacterial, viral, and parasitic infections, and cancer as described above. In each of these disease states, the presence of the offending agent stimulates TNF production which stimulates a corresponding increase in sTNFRI production. sTNFRI production is intended to reduce localized, as well as systemic, toxicity associated with elevated TNF levels and to restore immunologic homeostasis.

In tumor bearing hosts, over-production of sTNFRI may profoundly affect the course of disease, considering the critical role of TNF in a variety of anti-tumor immune responses (Reviewed in, Beutler and Cerami, *Ann. Rev. Immunol.* 7:625–655 (1989)). TNF directly induces tumor cell death by binding to the type I membrane-associated TNF receptor. Moreover, the death of vascular endothelial cells is induced by TNF binding, destroying the circulatory network serving the tumor and further contributing to tumor cell death. Critical roles for TNF in natural killer cell-and cytotoxic T lymphocyte-mediated cytolysis also have been documented. Inhibition of any or all of these effector mechanisms by sTNFRI has the potential to dramatically enhance tumor survival.

That sTNFRI promotes tumor survival, and that its removal enhances anti-tumor immunity, has been demonstrated. In an experimental mouse tumor model, sTNFRI production was found to protect transformed cells in vitro from the cytotoxic effects of TNF, and from cytolysis mediated by natural killer cells and cytotoxic T lymphocytes (Selinsky, et al., Immunol. 94: 88–93 (1998)). In addition, the secretion of sTNFRI by transformed cells has been shown to markedly enhance their tumorigenicity and persistence in vivo (Selinsky and Howell, unpublished). Moreover, removal of circulating sTNFRI has been found to provide clinical benefit to cancer patients, as demonstrated by human trials of Ultrapheresis as discussed above (Lentz, M. R., supra). These observations affirm the importance of this molecule in tumor survival, and suggest the development of methods for more specific removal of sTNFRI as promising new avenues for cancer immunotherapy.

The following examples are intended to illustrate but not limit the invention.

EXAMPLE 1

Production, Purification, and Characterization of the Immune System Inhibitor, Human sTNFRI The sTNFRI used in the present studies was produced recombinantly in cell culture. The construction of the eukaryotic expression plasmid, the methods for transforming cultured cells, and for assaying the production of sTNFRI by the transformed cells have been described (Selinsky, et al., supra). The sTNFRI expression plasmid was introduced into HeLa cells (American Type Culture Collection #CCL 2), and an sTNFRI-producing transfectant cell line was isolated by limiting dilution. This cloned cell line was cultured in a fluidized-bed reactor at 37° C. in RPMI-1640, supplemented with 2.5% (v/v) fetal bovine serum and penicillin/streptomycin, each at 100 micrograms per milliliter. sTNFRI secreted into the culture medium was purified by affinity chromatography on a TNF-Sepharose-4B affinity matrix essentially as described (Engelmann, et al., *J. Biol. Chem.* 265:1531–1536).

sTNFRI was detected and quantified in the present studies by capture ELISA (Selinsky, et al., supra). In addition, the biological activity of recombinant sTNFRI, i.e., its ability to bind TNF, was confirmed by ELISA. Assay plates were coated with human TNF-α (Chemicon), blocked with bovine serum albumin, and sTNFRI, purified from culture supernatants as described above, was added. Bound sTNFRI was detected through the sequential addition of biotinylated-goat anti-human sTNFRI, alkaline phosphatase-conjugated streptavidin, and ρ-nitrophenylphosphate.

EXAMPLE 2

Production of Absorbent Matrices

Binding partners used in the present studies include an IgG fraction of goat anti-human sTNFRI antisera (R&D Systems, Cat. #AF-425-PB) and a monoclonal antibody reactive with sTNFRI (Biosource International, Cat.#AHR3912). An additional monoclonal antibody, OT145 (Cat.#TCR1657), reactive with a human T cell receptor protein, was purchased from T Cell Diagnostics (now, Endogen) and was used as a control binding partner. Each of these respective binding partners was covalently conjugated to cyanogen bromide-activated Sepharose-4 B (Pharmacia Biotech), a macroporous bead which facilitates the covalent attachment of proteins. Antibodies were conjugated at 1.0 milligram of protein per milliliter of swollen gel, and the matrices were washed extensively according to the manufacturer's specifications. Matrices were equilibrated in phosphate buffered saline prior to use.

EXAMPLE 3

Depletion of the Immune System Inhibitor, sTNFRI, From Human Plasma Using Absorbent Matrices Normal human plasma was spiked with purified sTNFRI to a final concentration of 10 nanograms per milliliter, a concentration comparable to those found in the circulation of cancer patients (Gadducci, et al., supra). One milliliter of the spiked plasma was mixed with 0.25 milliliter of the respective absorbent matrices at and a plasma sample was removed at time=0. The samples were warmed rapidly to 37° C., and incubated with agitation for an additional 45 minutes. Plasma samples were removed for analysis at 15 minute intervals and, immediately after collection, were separated from the beads by centrifugation. Samples were analyzed by ELISA to quantify the levels of sTNFRI, and to permit the determination of the extent of depletion.

Figure 3:
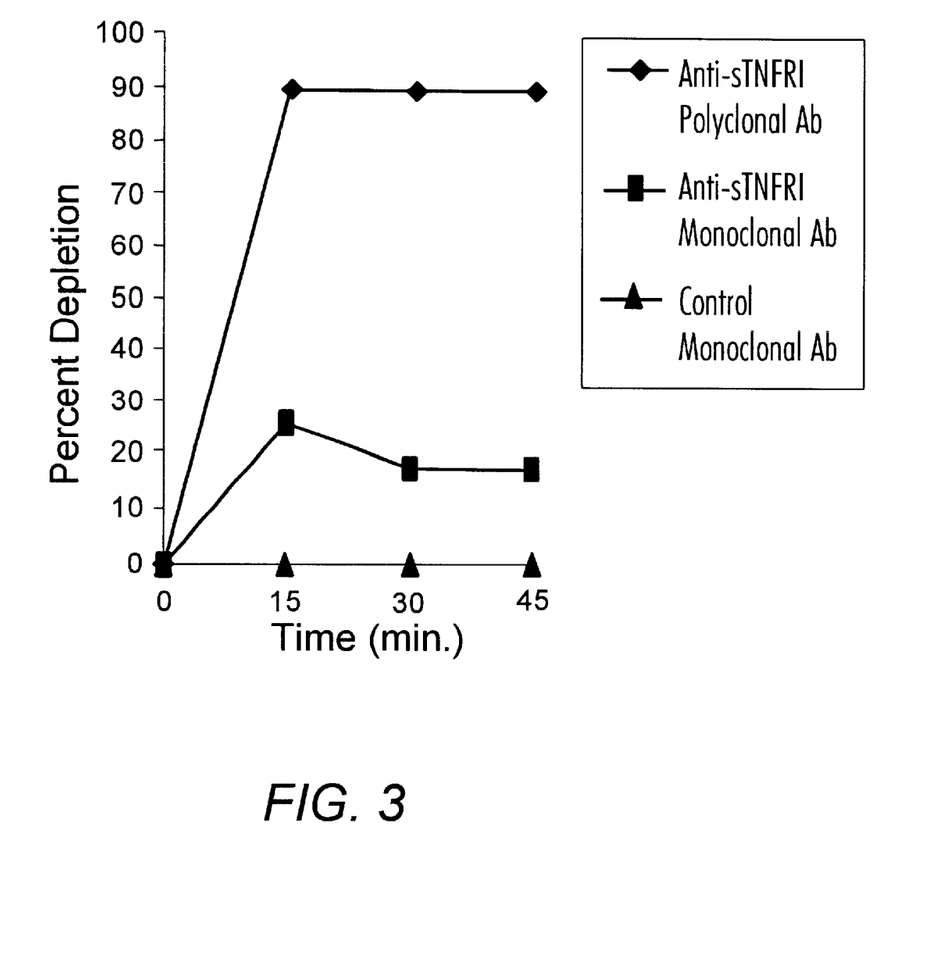
FIG. 3 shows the depletion of sTNFRI from human plasma by absorbent matrices constructed with monoclonal and polyclonal anti-sTNFRI antibody preparations, and with a monoclonal antibody of irrelevant specificity.

FIG. 3 shows the results of the sTNFRI depletion. The absorbent matrix produced with the goat anti-human sTNFRI polyclonal antibody rapidly removed the sTNFRI from the plasma sample; 90% of the sTNFRI was depleted within 15 minutes. The residual 1 nanogram per milliliter of sTNFRI in these samples is within the range of sTNFRI concentrations found in healthy individuals (Aderka, et al., supra; Chouaib, et al., *Immunol. Today* 12:141–145 (1991)). The matrix produced with the monoclonal anti-human sTNFRI antibody, in contrast, only removed approximately one-fifth of the plasma sTNFRI. The differences in the ability of these two matrices to deplete sTNFRI likely reflect the influence of avidity which is enabled by the heterogeneity of epitope specificities present in the polyclonal antibody preparation. The control matrix produced no reduction in sTNFRI levels, confirming the specificity of the depletion observed with the anti-sTNFRI antibody matrices.

Although the invention has been described with reference to the presently preferred embodiments, it should be understood that various modifications can be made without departing from the spirit of the invention. Accordingly, the invention is limited only by the following claims.

What is claimed is:

1. A method of stimulating an immune response in a mammal having a pathological condition, comprising:
   a. obtaining whole blood from the mammal;
   b. separating the whole blood into a cellular component and an acellular component or a fraction of the acellular component, wherein said acellular component or said fraction of the acellular component contains a targeted immune system inhibitor selected from the group consisting of soluble receptors for tumor necrosis factors α and β, interleukin-1 receptor antagonist, soluble receptors for interferon-γ, soluble receptors for interleukin-1, and soluble receptors for interleukin-6;
   c. contacting the acellular component or said fraction of the acellular component with a binding partner capable of specifically binding to said targeted immune system inhibitor;
   d. removing the binding partner bound to said targeted immune system inhibitor from said acellular component or said fraction of said acellular component to produce an altered acellular component or altered fraction of the acellular component having a reduced amount of the targeted immune system inhibitor;
   e. combining the cellular component with the altered acellular component or altered fraction of the acellular component to produce altered whole blood; and
   f. administering the altered whole blood to the mammal.

2. The method of claim 1, wherein the binding partner is attached to an inert medium to form an absorbent matrix.

3. The method of claim 2, wherein the binding partner is covalently joined to the inert medium.

4. The method of claim 2, wherein the inert medium is a hollow fiber.

5. The method of claim 2, wherein the inert medium is a macroporous bead.

6. The method of claim 2, wherein the inert medium is a cellulose-based fiber.

7. The method of claim 2, wherein the inert medium is a synthetic fiber.

8. The method of claim 2, wherein the inert medium is a flat or pleated membrane.

9. The method of claim 2, wherein the inert medium is a silicabased particle.

10. The method of claim 1, wherein said binding partner is a binding partner to which the targeted immune system inhibitor binds in nature.

11. The method of claim 10, wherein said binding partner is produced recombinantly.

12. The method of claim 1, wherein said binding partner is a fragment of a binding partner to which the targeted immune system inhibitor binds in nature, wherein said fragment specifically binds to said targeted immune system inhibitor.

13. The method of claim 12, wherein said fragment is produced recombinantly.

14. The method of claim 1, wherein said binding partner is a monoclonal antibody.

15. The method of claim 14, wherein said monoclonal antibody is produced recombinantly.

16. The method of claim 1, wherein said binding partner is a fragment of a monoclonal antibody that specifically binds to said targeted immune system inhibitor.

17. The method of claim 16, wherein said monoclonal antibody fragment is produced recombinantly.

18. The method of claim 1, wherein the acellular component or the fraction of said acellular component is in contact with a plurality of binding partners comprising a mixture of different monoclonal antibodies or fragments thereof, wherein said monoclonal antibodies or fragments thereof are capable of specifically binding to the targeted immune system inhibitor.

19. The method of claim 18, wherein the monoclonal antibodies, or fragments thereof, are produced recombinantly.

20. The method of claim 1, wherein the acellular component or the fraction of said acellular component is contacted with a plurality of binding partners comprising a mixture of different monoclonal antibodies or fragments thereof, wherein said monoclonal antibodies or fragments thereof are capable of specifically binding to a plurality of targeted immune system inhibitors.

21. The method of claim 20, wherein the monoclonal antibodies, or fragments thereof, are produced recombinantly.

22. The method of claim 1, wherein said binding partner is a polyclonal antibody preparation.

23. The method of claim 1, wherein said binding partner is comprised of fragments of a polyclonal antibody preparation that specifically bind to said targeted immune system inhibitor.

24. The method of claim 1, wherein the acellular component or the fraction of said acellular component is in contact with a plurality of binding partners comprising a mixture of different polyclonal antibody preparations or fragments thereof, wherein said polyclonal antibodies or fragments thereof are capable of specifically binding to the targeted immune system inhibitor.

25. The method of claim 1, wherein the acellular component or the fraction of said acellular component is in contact with a plurality of binding partners comprising a mixture of different polyclonal antibody preparations or fragments thereof, wherein said polyclonal antibodies or fragments thereof are capable of specifically binding to a plurality of targeted immune system inhibitors.

26. The method of claim 1, wherein the binding partner is a synthetic peptide.

27. The method of claim 26, wherein the synthetic peptide is conjugated to a carrier.

28. The method of claim 1, wherein the biological fluid is contacted with a plurality of binding partners comprising a mixture of synthetic peptides capable of specifically binding to the targeted immune system inhibitor.

29. The method of claim 28, wherein said mixture of synthetic peptides is conjugated to a carrier.

30. The method of claim 1, wherein the biological fluid is contacted with a plurality of binding partners comprising a mixture of synthetic peptides capable of specifically binding to a plurality of targeted immune system inhibitors.

31. The method of claim 30, wherein said mixture of synthetic peptides is conjugated to a carrier.

32. The method of claim 1, wherein steps (a) through (e) are repeated.

33. The method of claim 1, wherein the mammal is human.

34. The method of claim 1, wherein the mammal is non-human.

35. The method of claim 1, wherein the binding partner bound to the targeted immune system inhibitor is removed by mechanical means.

36. The method of claim 1, wherein the binding partner bound to the targeted immune system inhibitor is removed by chemical/biological means.

37. A method for stimulating an immune response in a mammal having a pathological condition, comprising:

a. obtaining a whole blood from a mammal;

b. separating the acellular component or a fraction of said acellular component of the whole blood from the cellular component of the whole blood, said acellular component or said fraction of the acellular component containing a targeted immune system inhibitor selected from the group consisting of soluble receptors for tumor necrosis factors $\alpha$ and $\beta$, interleukin-1 receptor antagonist, soluble receptors for interferon-$\gamma$, soluble receptors for interleukin-1, and soluble receptors for interleukin-6;

c. contacting the acellular component or fraction of said acellular component containing the targeted immune system inhibitor with at least one antibody capable of specifically binding to the targeted immune system inhibitor, wherein the antibody is attached to an inert medium to form an absorbent matrix;

d. removing the absorbent matrix comprising the antibody bound to the targeted immune system inhibitor from the acellular component or fraction of the acellular component to produce an altered acellular component or altered fraction of the acellular component;

e. combining the altered acellular component or altered fraction of the acellular component with the cellular component to produce an altered whole blood; and f. administering the altered whole blood to the mammal.

38. A method for stimulating an immune response in a mammal having a pathological condition, comprising:

(a) obtaining whole blood from a mammal;

(b) separating the acellular component of the whole blood or a fraction of the acellular component of the whole blood from the cellular component of the whole blood;

(c) contacting the acellular component or fraction of the acellular component with at least one antibody that specifically binds to soluble receptors for tumor necrosis factors $\alpha$ and $\beta$;

(d) isolating the at least one antibody bound to the soluble receptors for tumor necrosis factors $\alpha$ and $\beta$ from the acellular component or fraction of the acellular component to produce an altered acellular component or an altered fraction of the acellular component, respectively;

(e) combining the altered acellular component or the altered fraction of the acellular component with the cellular component to produce altered whole blood; and (f) administering the altered whole blood to the mammal.

39. The method of claim 38 wherein the at least one antibody is attached to an inert medium to form an absorbent matrix.

40. The method of claim 39, wherein the at least one antibody is covalently joined to the inert medium.

41. The method of claim 38, wherein said at least one antibody is a monoclonal antibody or a fragment of monoclonal antibody that specifically binds to said soluble receptors for tumor necrosis factors $\alpha$ and $\beta$.

42. The method of claim 38, wherein the acellular component or fraction of the acellular component is contacted with a plurality of antibodies comprising a mixture of different monoclonal antibodies or fragments thereof, wherein said monoclonal antibodies or fragments thereof specifically bind to said soluble receptors for tumor necrosis factors $\alpha$ and $\beta$.

43. The method of claim 38, wherein said at least one antibody is a polyclonal antibody preparation, or fragments of a polyclonal antibody preparation that specifically bind to said soluble receptors for tumor necrosis factors $\alpha$ and $\beta$.

44. The method of claim 38, wherein the whole blood is in contact with a plurality of antibodies comprising a mixture of different polyclonal antibody preparations or fragments thereof, wherein said polyclonal antibodies or fragments thereof specifically bind to said soluble receptors for tumor necrosis factors $\alpha$ and $\beta$.

* * * * *